(12) United States Patent
Maffietti

(10) Patent No.: US 10,508,079 B2
(45) Date of Patent: Dec. 17, 2019

(54) METHOD FOR PURIFICATION OF A CO2 STREAM

(71) Applicant: Casale SA, Lugano (CH)

(72) Inventor: Federico Maffietti, Como (IT)

(73) Assignee: Casale SA (CH)

( * ) Notice: Subject to any disclaimer, the term of this patent is extended or adjusted under 35 U.S.C. 154(b) by 0 days.

(21) Appl. No.: 15/764,705

(22) PCT Filed: Sep. 8, 2016

(86) PCT No.: PCT/EP2016/071226
§ 371 (c)(1),
(2) Date: Mar. 29, 2018

(87) PCT Pub. No.: WO2017/055052
PCT Pub. Date: Apr. 6, 2017

(65) Prior Publication Data
US 2018/0258035 A1  Sep. 13, 2018

(30) Foreign Application Priority Data

Sep. 30, 2015  (EP) .................................. 15187718

(51) Int. Cl.
*C07C 273/10* (2006.01)
*B01J 23/42* (2006.01)
(Continued)

(52) U.S. Cl.
CPC .......... *C07C 273/10* (2013.01); *B01D 53/265* (2013.01); *B01D 53/8668* (2013.01); *B01D 53/8671* (2013.01); *B01J 23/42* (2013.01); *B01J 23/44* (2013.01); *C01B 3/48* (2013.01); *C01B 32/50* (2017.08); *C01C 1/0447* (2013.01); *C01C 1/0488* (2013.01); *B01D 2255/1021* (2013.01); *B01D 2255/1023* (2013.01); *B01D 2257/108* (2013.01); *B01D 2257/704* (2013.01); *C01B 2203/0205* (2013.01); *C01B 2203/0283* (2013.01); *C01B 2203/0415* (2013.01); *C01B 2203/0475* (2013.01); *C01B 2203/068* (2013.01); *C01B 2210/0004* (2013.01);
(Continued)

(58) Field of Classification Search
None
See application file for complete search history.

(56) References Cited

U.S. PATENT DOCUMENTS 2,999,008 A    9/1961  Diebold
7,521,483 B2   4/2009  Davey et al.

FOREIGN PATENT DOCUMENTS

DE    26 04 054 A    12/1976
EP    0 952 111 A1   10/1999
(Continued)

OTHER PUBLICATIONS

International Search Report dated Oct. 11, 2016 in connection with PCT/EP2016/071226.
(Continued)

*Primary Examiner* — Amy C Bonaparte
(74) *Attorney, Agent, or Firm* — Akerman LLP

(57) ABSTRACT

A process for removing hydrogen and methanol from a CO2 stream which contains hydrogen and methanol as contaminants, wherein hydrogen and methanol are removed by contacting the CO2 stream with a catalyst which oxidizes hydrogen to water and methanol to carbon dioxide, obtaining a purified CO2 stream.

10 Claims, 2 Drawing Sheets

(51) Int. Cl.
  *B01J 23/44*  (2006.01)
  *C01C 1/04*  (2006.01)
  *B01D 53/86*  (2006.01)
  *C01B 32/50*  (2017.01)
  *B01D 53/26*  (2006.01)
  *C01B 3/48*  (2006.01)

(52) U.S. Cl.
  CPC ............... *C01B 2210/0053* (2013.01); *C01B 2210/0068* (2013.01)

(56) References Cited

FOREIGN PATENT DOCUMENTS

| | | | |
|---|---|---|---|
| EP | 2 502 881 A1 | 9/2012 | |
| WO | 00/47309 A1 | 8/2000 | |
| WO | 2010/129413 A1 | 11/2010 | |
| WO | 2011/020618 A1 | 2/2011 | |

OTHER PUBLICATIONS

International Preliminary Report on Patentability issued in connection with PCT/EP2016/071226, dated Feb. 12, 2018.
Written Opinion of the International Searching Authority issued in connection with PCT/EP2016/071226, dated Apr. 6, 2017.
Response to Written Opinion filed Aug. 31, 2017 in connection with PCT/EP2016/071226.
Response to International Preliminary Report on Patentability filed Jan. 29, 2018 in connection with PCT/EP2016/071226.
Klaus Noelker et al., "Methanol Emission from Ammonia Plants and its Reduction", 58th Annual Safety in Ammonia Plants and Related Facilities Symposium, Frankfurt, Germany, Aug. 26, 2013, http://www.thyssenkrupp-industrial-solutions.com/fileadmin/documemts/publications/AlChE-Ammonia-2013/Reduction_of_MethanolEmission_2013_paper.pdf, pp. 5, 7; figure 2.

METHOD FOR PURIFICATION OF A CO2 STREAM

This application is a national phase of PCT/EP2016/071226, filed Sep. 8, 2016, and claims priority to EP 15187718.0, filed Sep. 30, 2015, the entire contents of both of which are hereby incorporated by reference.

FIELD OF THE INVENTION

The invention relates to a method for purification of a carbon dioxide stream from hydrogen and methanol. The invention can be applied advantageously to the purification of a CO2 feed for the synthesis of urea.

PRIOR ART

Urea is synthesized by reacting ammonia and carbon dioxide in a urea plant. A discussion of the various processes and related plants for the urea production can be found in literature, e.g. Ullmann's Encyclopedia of Industrial Chemistry, Wiley-VCH Verlag.

The synthesis of urea is a complex process which is sensitive to contaminants and requires feeds of ammonia and carbon dioxide of a high purity. In this respect, the integrated ammonia-urea plants suffer the drawback of a contamination of the carbon dioxide feed with hydrogen and methanol.

In an integrated ammonia-urea facility, both ammonia and carbon dioxide for the urea synthesis come from a tied-in ammonia plant. Ammonia is produced by reacting a make-up gas obtained by reforming a hydrocarbon and carbon dioxide is obtained from purification of the raw make-up gas. A common method for removal of CO2 is washing with methanol or aqueous methanol solutions, which leaves some methanol (e.g. about 1000 ppm) in the so obtained CO2 stream. The raw make-up gas contains hydrogen and, hence, the CO2 stream produced by the purification of said gas typically contains also some hydrogen.

Both methanol and hydrogen are highly detrimental to the synthesis of urea. Methanol tends to accumulate in the urea plant leading to formation of polymeric compounds, which negatively affect the synthesis of urea and worsen the performances of the plant. In particular, one of the detrimental effects of said compounds is fouling of equipment of the water treatment section, such as heat exchangers and hydrolyzer. Hydrogen is dangerous as it may form an explosive mixture with oxygen, which is present as passivating means.

Therefore, methods for removing hydrogen and methanol from the CO2 feed have been proposed in the art. According to the prior art, hydrogen is removed by oxidation with air or oxygen in a catalytic reactor while methanol, in virtue of its polarity, is removed by water washing in another apparatus.

The above process has some disadvantages. First of all, it involves two steps which are carried out in two separate units, thus requiring big and complex equipment. Further, removal of methanol by washing requires large flowrates of water and process condensate.

SUMMARY OF THE INVENTION

The invention aims to solve the above shortcomings of the prior art. In greater detail, the invention aims to provide a method for removing hydrogen and methanol from a CO2 stream, which allows, over the prior art, constructional simplicity with advantages in terms of cost and reduced consumption of water.

This aim is reached with a method for removing hydrogen and methanol from a CO2 stream containing hydrogen and methanol as contaminants, which is characterized in that hydrogen and methanol are removed by contacting the CO2 stream with a catalyst which oxidizes hydrogen to water and methanol to carbon dioxide, thus obtaining a purified CO2 stream.

The term of CO2 stream denotes a stream which predominantly contains carbon dioxide.

According to the process of the invention, the same catalyst for oxidizing hydrogen to water is used for oxidizing methanol to carbon dioxide. Then, hydrogen and methanol can be removed from the CO2 stream in a single catalytic reactor.

Preferably, a platinum-based catalyst or palladium-based catalyst is used.

Preferably, the purified CO2 stream contains 10 ppm (vol) or less of hydrogen. Preferably, the purified CO2 stream contains a residual 200 ppm (vol) or less of methanol, more preferably less than 100 ppm (vol). Lower concentrations can be reached by suitably dimensioning the amount of catalyst. The above ppm concentrations denoted by ppm (vol) refer to volume fraction.

In a preferred embodiment of the invention, said CO2 stream is mixed with a suitable amount of oxidant to support the above oxidation. In some embodiments, said oxidant is in a sufficient amount to provide also a required amount of oxygen to act as passivating agent. For example, an embodiment of the invention provides that at least part of the purified CO2 stream feeds a urea synthesis process where urea is produced from ammonia and CO2 and, in that case, it is preferred to introduce some oxygen to passivate the urea reactor and protect against corrosion.

According to preferred embodiments, said catalytic oxidation of hydrogen to water and of methanol to carbon dioxide is carried out at a high pressure of at least 20 bar; however said catalytic oxidation can also be carried out at lower pressures, for example 10-20 bar. A high pressure is generally preferred to reduce volumetric rate and size of the equipment.

In preferred embodiments, water and carbon dioxide obtained by the above catalytic oxidation are cooled in a downstream cooler with formation of a two phase stream, which is introduced into a phase separator for separation of water and carbon dioxide.

Hereinafter, said catalytic reactor, cooler and separator are globally referred to as hydrogen and methanol removal section.

In some embodiments the CO2 stream is extracted from the front-end of the ammonia section of an ammonia-urea integrated plant. An ammonia-urea integrated plant basically includes an ammonia section and a urea section. The ammonia section comprises a front-end which converts a hydrocarbon source (such as natural gas) into a make-up gas, by catalytic reforming, and a synthesis loop where the make-up gas is converted to ammonia. At least part of said ammonia reacts in the urea section to produce urea. Urea is synthesized at a high pressure, typically around 150 bar.

The front end usually comprises a reforming section followed by a purification section performing at least shift conversion and CO2 removal. The front-end operates at a pressure usually around 30 bar. A CO2 stream is originated by the above mentioned removal of CO2 from the shifted gas. Said CO2 stream can be purified according to the invention for a subsequent use as reactant for the synthesis of urea. To this purpose the CO2 stream, which is delivered at a low pressure, need be raised to the urea synthesis pressure. Due to the considerable compression ratio, this task requires typically a multi-stage compression.

According to a preferred embodiment of the present invention, said CO2 stream is compressed to a first pressure which is intermediate between the pressure of the CO2 stream and the pressure of the synthesis of urea. The catalytic removal of hydrogen and methanol is carried out at said first pressure. For example said first pressure is about 10 to 20 bar. Then, at least part of the so obtained purified CO2 stream is raised to the pressure of urea synthesis and used to produce urea.

The first compression can be carried out in one or more first stage(s) of the multi-stage compression and the second compression is carried out in one or more remaining stages of said multi-stage compression. Accordingly, the inventive catalytic removal of hydrogen and methanol is highly integrated with the required compression of CO2 for synthesis of urea.

In other words, the catalytic oxidation of hydrogen to water and methanol to carbon dioxide is performed advantageously at the pressure of an intermediate stage of the multi-stage compression of CO2.

A reactor for the removal of hydrogen and methanol from a CO2 stream, characterized by containing a catalyst suitable to oxidize hydrogen to water and methanol to carbon dioxide, is also an object of the invention. An ammonia plant and particularly an ammonia-urea integrated plant including said reactor are also object of the present invention.

Some of the advantages of the process of the invention over the traditional methods have been discussed above. A major advantage is that carbon dioxide is purified from hydrogen and methanol with a single process step in a single reactor. The elimination of a washing column for the removal of methanol results in a significant saving of the water flowrates and process condensate Another advantage is that oxidation of methanol to carbon dioxide results in a greater amount of carbon dioxide for a further use, particularly for the synthesis of urea.

The advantages will emerge even more clearly with the aid of the detailed description below, relating to a preferred embodiment.

DESCRIPTION OF A PREFERRED EMBODIMENT

Figure 1:
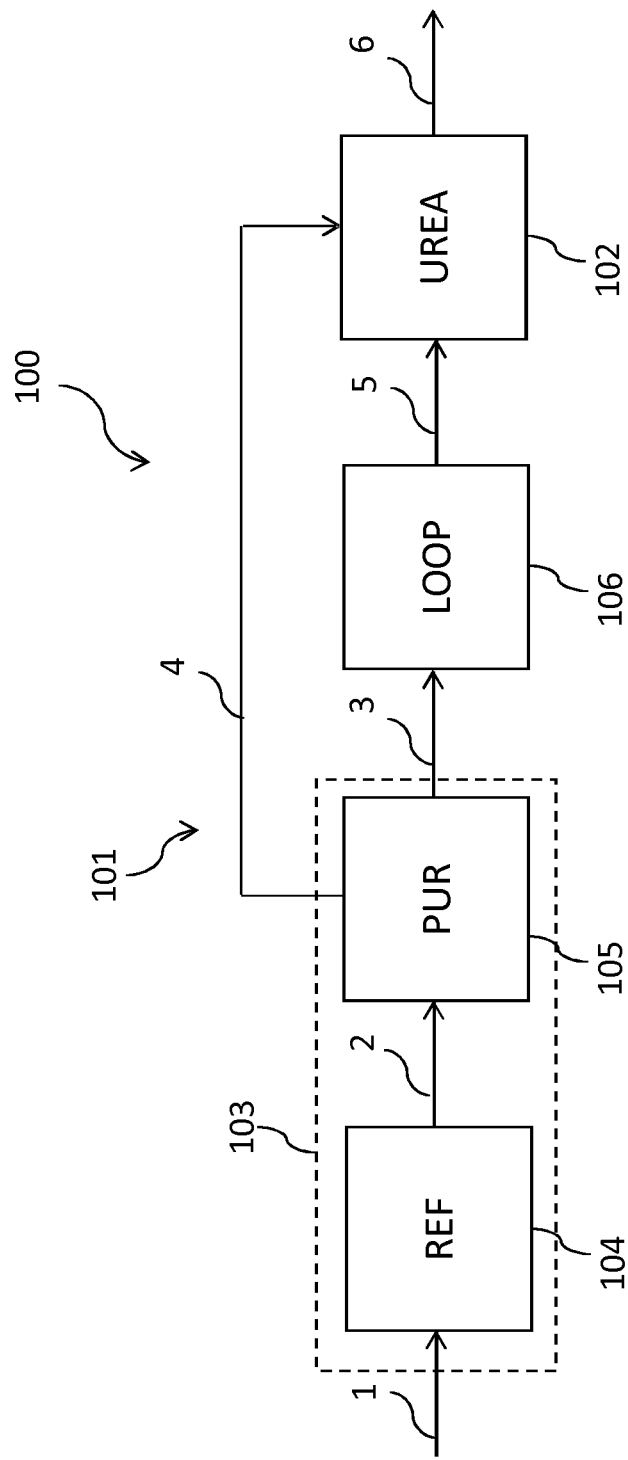
FIG. 1 shows a block scheme of an ammonia-urea integrated plant which can include an embodiment of the invention.

FIG. 1 illustrates a block scheme of an ammonia-urea integrated plant 100 comprising an ammonia section 101 and a urea section 102.

The ammonia section 101 comprises a front-end section 103 and a synthesis loop 106. The front-end section 103 essentially comprises a reforming section 104 for the conversion of a hydrocarbon feedstock 1 into a raw synthesis gas 2 and a purification section 105 for the purification of said raw gas into a make-up gas 3 and separation of a carbon dioxide stream 4. The synthesis loop 106 essentially comprises a reactor, a separator and a purge recovery unit (not shown) and provides an ammonia product 5.

Said carbon dioxide stream 4 and ammonia 5 are fed to the urea section 102 at a suitable pressure, where they react to provide urea 6. In particular, carbon dioxide 4 is suitably compressed in a gas compressor 111 (shown in FIG. 2) to reach the synthesis pressure, for example around 150 bar.

The urea section 102 can implement any of the known processes for the synthesis of urea, including e.g. the CO2 stripping process, the self-stripping process or another.

Figure 2:
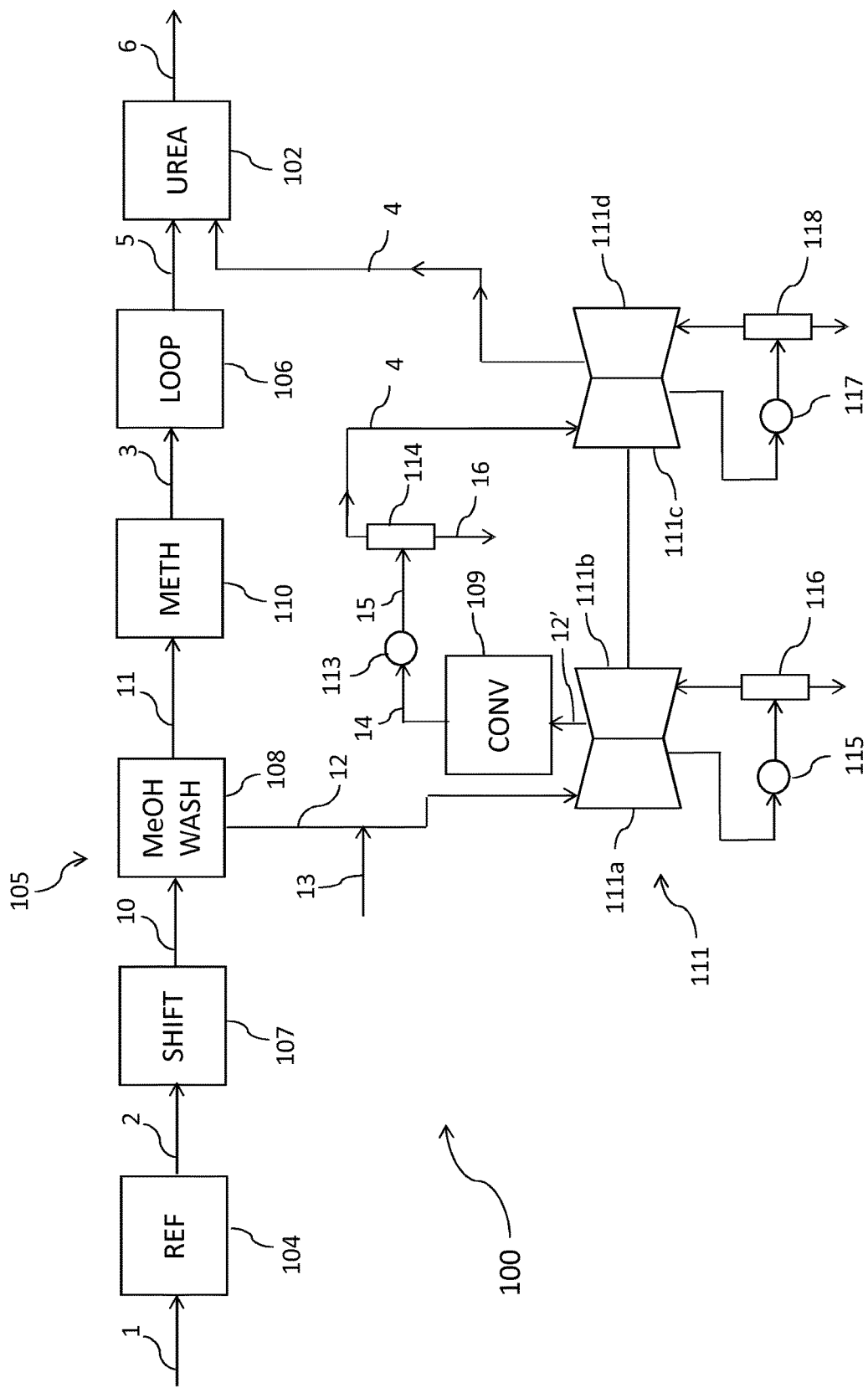
FIG. 2 shows in greater detail the plant of FIG. 1 and the related gas purification section according to an embodiment of the invention.

According to FIG. 2, the purification section 105 of the front-end section includes a CO-shift converter 107, a CO2-removal unit 108, a catalytic converter 109 and a methanator 110. The unit 108 removes carbon dioxide from shifted gas 10 by a methanol washing, producing a CO2-depleted gas 11 and a CO2 stream 12 also containing some methanol and residual hydrogen.

The CO2-depleted gas 11 is fed to the methanator 110 wherein residual carbon monoxide and hydrogen are converted into methane producing the make-up gas 3.

The CO2 stream 12 is mixed with air 13 and sent to the converter 109 via the first two stages 111a and 111b of the gas compressor 111, an inter-stage cooler 115 and a separator 116. The resulting CO2 stream 12' enters the converter 109 under pressure.

The so pressurized CO2 stream 12' reacts over a platinum or palladium-based catalyst contained in the converter 109, to provide a purified CO2 stream 14 containing water and carbon dioxide (i.e. oxidation products). Said purified stream 14 is withdrawn from the top of said catalytic reactor 109 and passed through a cooler 113, wherein at least some of the water is condensed. The resulting two phase stream 15 is passed through a phase separator 114, to obtain a gaseous stream of dry purified carbon dioxide 4 and a condensate 16. Said dry and purified carbon dioxide 4 is then delivered to the urea section 102 by the remaining stages 111c and 111d of the compressor 111, including a further intercooler 117 and separator 118.

Hence it can be appreciated that the converter 109 is integrated with the multi-stage compressor 111, running at the intermediate pressure of delivery of the stage 111b.

The CO2 stream 12 obtained from the washing unit 108 is purified from methanol and hydrogen, leading to a clean CO2 current 4 suitable to feed the urea synthesis.

The invention claimed is:

1. A process for removing hydrogen and methanol from a $CO_2$ stream which contains hydrogen and methanol as contaminants,
   wherein hydrogen and methanol are removed by contacting said $CO_2$ stream with a catalyst which oxidizes hydrogen to water and methanol to carbon dioxide, obtaining a purified $CO_2$ stream,
   wherein at least part of said purified $CO_2$ stream, after removal of methanol and hydrogen, is fed into a urea synthesis process of an ammonia-urea integrated plant, and
   wherein said $CO_2$ stream containing hydrogen and methanol is extracted from an ammonia section of said ammonia-urea integrated plant, wherein urea is produced at a urea synthesis pressure;
   said $CO_2$ stream containing hydrogen and methanol is extracted at a pressure lower than said urea synthesis pressure;
   the $CO_2$ stream containing hydrogen and methanol is compressed to a first pressure intermediate between said pressure of extraction and said urea synthesis pressure; and the removal of hydrogen and methanol is carried out at said first pressure; and at least part of the so obtained purified $CO_2$ stream is further compressed to said urea synthesis pressure and is fed to said urea synthesis process.

2. The process according to claim 1, wherein said step of contacting the $CO_2$ stream with said catalyst is performed in a single catalytic reactor.

3. The process according to claim 1, wherein said catalyst is a platinum-based or palladium-based catalyst.

4. The process according to claim 1, wherein the purified $CO_2$ stream, after removal of hydrogen and methanol, contains no more than 10 ppm (vol) of hydrogen.

5. The process according to claim 1, wherein the purified $CO_2$ stream, after removal of hydrogen and methanol, contains no more than 200 ppm (vol) of methanol.

6. The process according to claim 1, wherein said $CO_2$ stream containing hydrogen and methanol is mixed with an amount of oxidant such as to provide at least an amount of oxygen required for oxidation of hydrogen to water and methanol to carbon dioxide.

7. The process according to claim 1, wherein oxidation of hydrogen to water and methanol to carbon dioxide is carried out at a pressure of at least 20 bar or greater.

8. The process according to claim 1, wherein said $CO_2$ stream containing hydrogen and methanol is mixed with an oxidant in a sufficient amount to provide oxygen for oxidation of hydrogen and methanol, and further oxygen for use as passivating agent in the urea synthesis process.

9. The process according to claim 1, wherein the first compression is carried out in one or more first stage(s) of a multi-stage compressor and the second compression is carried out in one or more remaining stages of said compressor.

10. The process according to claim 1, wherein water obtained by oxidation of hydrogen is separated from the purified carbon dioxide stream by condensation in a separator at said first pressure.

* * * * *